United States Patent
Emerson et al.

(10) Patent No.: US 9,370,637 B2
(45) Date of Patent: Jun. 21, 2016

(54) SENSORY DEVICE USEFUL IN BRINGING A PATIENT NEUROLOGICAL OR PSYCHOLOGICAL RELIEF

(71) Applicant: Hospice Of Dayton, Dayton, OH (US)

(72) Inventors: Kathleen Emerson, Dayton, OH (US); Kent Anderson, Beavercreek, OH (US); Mary Murphy, Centerville, OH (US)

(73) Assignee: The Hospice of Dayton, Incorporated, Dayton, OH (US)

( * ) Notice: Subject to any disclaimer, the term of this patent is extended or adjusted under 35 U.S.C. 154(b) by 401 days.

(21) Appl. No.: 13/709,215

(22) Filed: Dec. 10, 2012

(65) Prior Publication Data

US 2013/0165740 A1 Jun. 27, 2013

Related U.S. Application Data

(60) Provisional application No. 61/578,302, filed on Dec. 21, 2011.

(51) Int. Cl.
*A61M 21/00* (2006.01)
*A61M 21/02* (2006.01)

(52) U.S. Cl.
CPC ......... *A61M 21/02* (2013.01); *A61M 2021/005* (2013.01); *A61M 2205/50* (2013.01)

(58) Field of Classification Search
CPC ............ A61M 21/02; A61M 2205/50; A61M 2021/005
USPC ............................... 600/26–28; 128/897–899
See application file for complete search history.

(56) References Cited

U.S. PATENT DOCUMENTS

| | | | | |
|---|---|---|---|---|
| 3,826,250 | A | * | 7/1974 | Adams ............................ 601/16 |
| 4,553,534 | A | * | 11/1985 | Stiegler ........................... 601/15 |
| 4,762,131 | A | | 8/1988 | Okuda |
| 5,681,259 | A | * | 10/1997 | August ........................... 600/27 |
| 6,758,566 | B2 | | 7/2004 | Goulden et al. |
| 6,870,673 | B2 | * | 3/2005 | Cromer et al. ................ 359/450 |
| 7,177,079 | B2 | | 2/2007 | Cromer et al. |
| 2002/0038073 | A1 | * | 3/2002 | August ........................... 600/27 |
| 2010/0309391 | A1 | * | 12/2010 | Plut ...................... H04N 9/3147 348/756 |
| 2010/0331606 | A1 | * | 12/2010 | Wong et al. ..................... 600/27 |
| 2012/0323591 | A1 | * | 12/2012 | Bechtel et al. .................... 705/2 |
| 2013/0063009 | A1 | * | 3/2013 | Hayne ..................... A47D 1/00 312/237 |

OTHER PUBLICATIONS

Altun A. et al. "Impaired Nocturnal Synthesis of Melatonin in Patients With Cardiac Syndrome X", published in Neuroscience Letters, vol. 19; 327(2): 143-5 (2002).
Claustrat, Bruno, et al. "The Basic Physiology and Patholphysiology of Melatonin", published by Elsevier Science Ireland Ltd., Sleep Medicine Reviews, vol. 9, pp. 11-24. (2005).

(Continued)

*Primary Examiner* — Navin Natnithithadha
*Assistant Examiner* — Sunita Reddy
(74) *Attorney, Agent, or Firm* — Wood, Herron & Evans, LLP

(57) ABSTRACT

A method and apparatus which generates an image and particularly a celestial or a natural image having embedded movement that is useful in relieving conditions such as patient angst, depression and the like. The apparatus may include a control panel for adjusting the image and the movement based on the patient's condition or response to the image.

7 Claims, 2 Drawing Sheets

(56) References Cited

OTHER PUBLICATIONS

Inouye, M.D., M.P.H. "Delirium in Older Persons", published in The New England Journal of Medicine, vol. 354, pp. 1157-1165. (2006).

Brusco, Luis I. et al. "Melatonin Treatment Stabilizes Chronobiologic and Cognitive Symptoms in Alzheimer's Disease", published in Neuroendocrinology Letters, vol. 21, pp. 39-42. (2000).

Hotz G., et al. Snoezelen: A Controlled Multi-Sensory Stimulation Therapy for Children Recovering From Severe Brain Injury. Brain Injury. 20(8): 879-888 (2006).

St. James J. Snoezelen' rooms soothe patients at Mesquite Retirement facility. Available at: E:\'Snoezelen' rooms soothe patients at Mesquite retirement facility wfaa_com Dallas—Fort Worth.mht. Accessed Sep. 23, 2011.

Harada, Tetsuo, "Effects of Evening Light Conditions on Salivary Melatonin of Japanese Junior High School Students", published by Journal of Circadian Rhythms. (2004).

Tsunoda, Mihoko, et al., "Effects of Light and Sleep Stages on Heart Rate Variability in Humans", published by in Psychiatry and Clinical Neurosciences, vol. 55, pp. 285-286. (2001).

Schulz, Pierre et al. "Neurobiology of Circadian Systems", published by CNS Drugs, 23 Suppl. 2: 3-13. (2009).

"Can You Imagine 5105 Laser Stars" from online catalog of Smarthome, www.smarthome.com/46488/Can-You-Imagine-5105-Laser-Stars/p.aspx (retrieved from the internet on Feb. 14, 2014).

"Instructions for Laser Stars" by Can You Imagine (published at least as early as Nov. 2010).

* cited by examiner

SENSORY DEVICE USEFUL IN BRINGING A PATIENT NEUROLOGICAL OR PSYCHOLOGICAL RELIEF

FIELD

The present invention relates to a therapeutic method and apparatus for relaxing a patient or relieving patient malaise in a health care setting. More specifically, the present invention relates to a method and apparatus for projecting an image such as a celestial image or a natural image on a surface for observation by the patient where the image changes or moves internally to the image in a manner that is controlled so as to enhance the benefit to the patient.

BACKGROUND

Observational studies assessing physiological, cognitive, and behavioral changes in a patient have shown that certain visual therapies are useful and effective for providing relaxation and/or sleep enhancement for patients receiving hospital care. Unless otherwise indicated, the term "hospital care" as used herein means health care in any controlled setting such as a hospital, clinic, nursing home, assisted living facility, hospice, etc. even including a room in the home in which a patient may be cared for.

Health conditions, including a wide range of mental and physical ailments, can force patients to spend extended periods of time in health care facilities. While in these facilities patients can become bored, depressed, or agitated and anxious, any or all of which may lead to negative mental health and hindered recovery. These patients may experience sever depression and/or anxiety. Additionally, they may become frustrated and outwardly aggressive or abusive.

One system that has been proposed in order to counter patient malaise is disclosed in U.S. Pat. No. 7,177,079 to Cromer et al. The '079 patent describes a system and method for providing a biosynchronized therapy that creates a therapeutic environment and stimulations that are sensitive to psychological and sensory human issues. The therapeutic environment is reported to reduce stress for the patient so that other forms of treatment are enhanced and benefitted. Other systems are disclosed in U.S. Pat. No. 5,681,259 and U.S. Pat. No. 3,826,250 to Adams.

DETAILED DESCRIPTION

Figure 1:
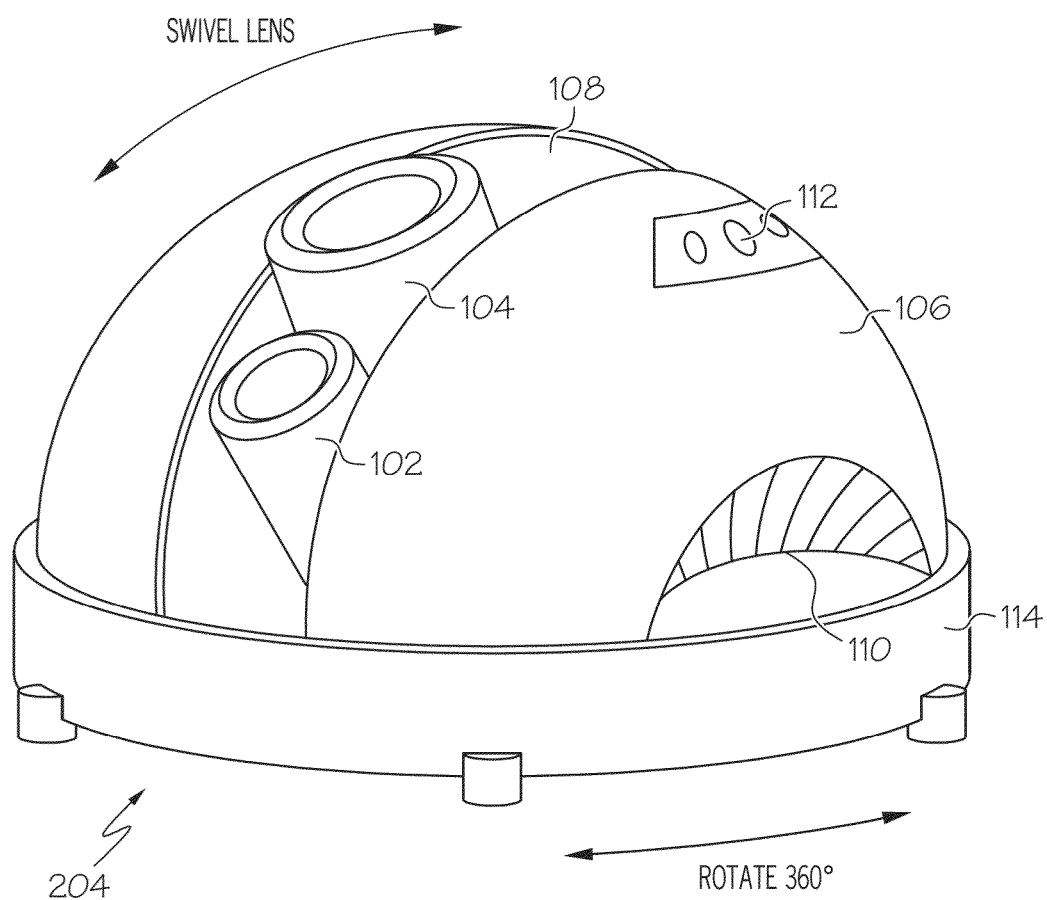
FIG. 1 is a perspective view of a sensory device useful in practicing certain embodiments of the invention.

As shown in FIG. 1, in one embodiment, the apparatus 100 may include two or more projectors 102, 104. The first projector 102 may project a first pattern or image component, such as an array of points of light representing a night sky. In one embodiment the first pattern or image may be formed by directing a laser, such as a green laser, through a rotating lens surface or, preferably, through a holographic film. The second projector 104 may project a second pattern or image component, such as clouds or celestial bodies, e.g., galaxies. In one embodiment, the second pattern or image may be formed using an array of blue and/or white LEDs in which the blue and/or white LEDs may be individually and selectively actuated. These patterns are provided as illustrations. In fact each projector may project one or more patterns or image components that in combination provide an image. The pattern or component image projected by at least one of the projectors will move with respect to the other. This quality is herein referred to as "embedded movement."

The image is a celestial image in one embodiment. The term "celestial image" as used herein includes any image of the heavens, skies or cosmos such as images including stars, clouds, star clusters or galaxies, shooting stars, novas, planets, comets, or other celestial objects, such as those normally occurring in the night sky or viewed telescopically including images that simulate images obtained using the Hubble telescope. In another embodiment the image may be a nature image such as a sunrise, sunset, moonrise, or moonset or other natural image capable of accommodating embedded movement.

The first and second projectors 102, 104 may be mounted in a housing 106. This housing 106 may include a central opening 108 through which the projectors 102, 104 extend. In the illustrated embodiment the opening 108 is a channel. Air vents 110 may be provided for heat dissipation. Also located on the housing 106 are a number of controls 112 or a control panel for the purpose described below. The housing 106 may be constructed of plastic, fiberglass, metal, or any other suitable material and may be dome-shaped as shown in FIG. 1 or may be of any other appropriate shape. In one embodiment, blue and/or white diodes project light through a first rotating lensed surface and a green laser projects through a second rotating lensed surface. The rotating lensed surfaces may be rotated by a single motor with a dual gear drive or through a pair of motors. The device may include a logic device to drive the rotating lenses to produce a variety of different image effects including controlling the relative movement of the first and second lenses.

According to one embodiment, the housing 106 of the apparatus 100 rotates about a base 114. The base 114 may be weighted to stabilize the device and may be provided with non-slip rubber feet. The housing 106 may rotate completely about the base 114 so that the patterns projected by projectors 102, 104 rotate. By pivoting the projectors 102 and/or 104 in the opening 108, the projected patterns may be viewed on the ceiling or one or more walls in the room. The projectors 102, 104 may be movable to a variety of azimuthal angles to project their patterns to a predetermined elevation. According to one embodiment, the first and second projectors 102, 104 are movable together along a single channel 108 so as to be fixed relative to one another. According to an alternative embodiment, the projectors 102, 104 are movable relative to one another along two or more channels 108. As a further alternative, the projectors 102, 104 may be movable separately in a single channel. Each projector 102, 104 may further be rotatable about an axis of projection so as to create the illusion of a spinning or rotating pattern. Each projector 102, 104 may also include a variety of colors and may be focusable to a preferred level of clarity.

In one embodiment, the apparatus 100 is controllable so as to project two or more patterns or component images in a variety of colors and rotational speeds at a variety of locations and angles throughout the room. The projected patterns or component images can be characterized based on their make up (e.g., light points or star clusters or galaxies), their color and, more particularly, the color of the moving component such as a point light source, and its rate of movement. The pattern or component image projected from each of the projectors 102, 104 may vary in intensity and sharpness as well.

Figure 2:
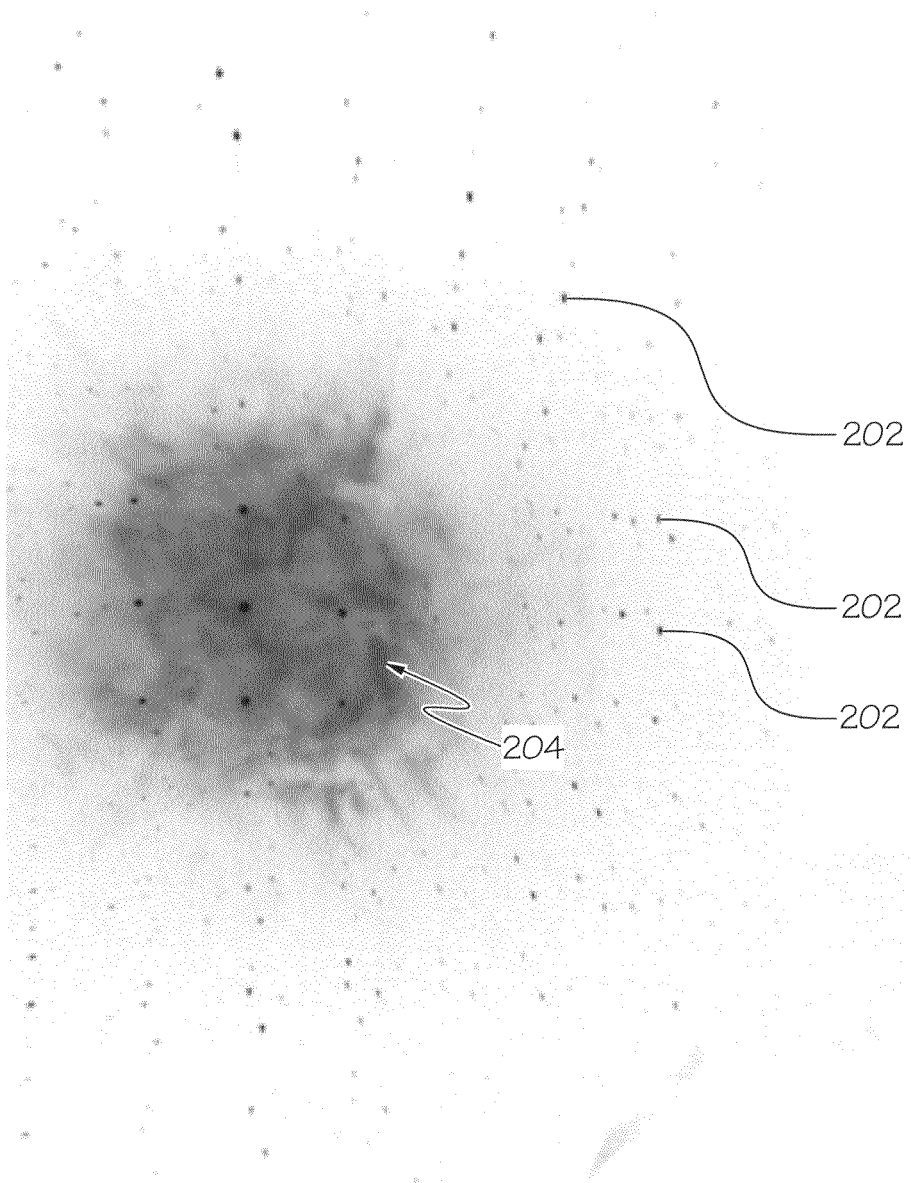
FIG. 2 is one example of a celestial image in accordance with one embodiment of the invention.

In a particular embodiment illustrated in FIG. 2, one of the projectors project laser or point light sources 202. It has been found that these sources are typically blue or green. While it may not always be the case, with many patients red point lights have not been found to be relaxing. The other projector projects a background pattern 204 such as cloud designs or star clusters or arcs.

One manifestation of the invention is based on the observation that there appears to be a correlation between the color and motions of the patterns 202 and 204 and the amount of relief brought to a patient depending upon the patient's psychological or neurological condition. This may vary from patient to patient. If a patient is anxious, a certain pattern of movement of an image may bring him or her more relief than others. This also may be true for conditions such as moribund restlessness where a patient may be afraid to sleep for fear of dying. It may also be useful with patients suffering from schizophrenia, depression, Alzheimer's disease, etc.

Accordingly, in one embodiment of the invention, the sensory device may include a microprocessor that is programmed or programmable with image patterns or component images including the composition of the image and the rate at which one pattern or component moves with respect to another pattern or component image. The control panel mentioned above may be designed to allow the user to select the components that make up a celestial image, e.g., the first pattern, the second pattern, the speed and direction of movement and the brightness and sharpness. In a particular embodiment, the control panel may have preset switches or an interface that provide pre-designed celestial images having embedded movement. In still another embodiment, the switches or interface may identify certain patient conditions such as anxiety, depression, agitation, and other psychotic or psychological conditions and based on clinical studies and/or health care experience the device will be programmed with one or more celestial images having embedded movements that may be more effective than others in providing the patient with relief.

As an illustration of the utility of the device, an 81 year old male with septicemia, recurrent urinary tract infections, pneumonia, diabetes, chronic obstructive pulmonary lung disease (COPD) and dementia was restless, anxious and agitated and having serious sleeping difficulties. His heart rate was 108, respiration was 30 per minute. His room was darkened and the sensory device was activated. Within 20 minutes he was sleeping, his heart rate was 78 and his respiration was 18 per minute. An hour and a half later with the device still running, after being given mouth and pericare, he fell back to sleep, his heart rate was 86 and his respiration was 14.

Having described the invention in detail and with respect to specific embodiments thereof, it will be apparent that numerous modifications are possible without departing from the spirit and scope of the following claims.

What is claimed is:

1. A method for treating a patient comprising:
   diagnosing the patient's physiological or neurological condition based at least in part on symptoms exhibited by the patient;
   correlating the patient's response to at least a first projected image with respect to the patient's condition, the image being formed from at least a first pattern or component and a second pattern or component, at least one of the patterns or components moving relative to the other patterns or components;
   selecting the first projected image or another image for projection from a projector apparatus based on the patient's response to the first image or based on the patient's condition,
   the projector apparatus comprising at least a first projector device for projecting the first pattern or component image onto a surface and a second projector device for projecting the second pattern or component onto the surface; and
   projecting the selected image with the projector apparatus so that the selected image and the relative movement associated with the selected image can be viewed by the patient;
   wherein the first projector device operates with a first light source, and the second projector device operates with a second light source;
   wherein the first light source comprises a laser, and the second light source comprises an array of light emitting diodes; and
   wherein the first pattern or component of the image is formed by directing the laser through a rotating lens surface or a holographic film; and the second pattern or component of the image is formed using the array of light emitting diodes that are individually and selectively actuated.

2. The method of claim 1, further comprising:
   periodically observing the patient's response to the projected image;
   selecting a different image with embedded movement; and
   projecting the different image so that the different image and the embedded movement can be viewed by the patient.

3. The method of claim 2 wherein the first image or the different image is a celestial image that includes a background pattern as the first pattern and a plurality of light points as the second pattern, and the background pattern moves with respect to some or all of the light points.

4. The method of claim 3 wherein the light points are blue and/or green and simulate stars or celestial bodies and the background pattern includes images or simulations of clouds or galactic patterns.

5. The method of claim 2 wherein a rate and/or direction of the embedded movement of the patterns is adjusted based upon the condition of the patient to reduce restlessness or agitation.

6. The method of claim 1 wherein the embedded movement includes azimuthal movement and/or rotational movement.

7. The method of claim 6 wherein the movement is movement of a plurality of light points.

* * * * *